United States Patent [19]

Amstutz et al.

[11] 4,123,806
[45] Nov. 7, 1978

[54] TOTAL HIP JOINT REPLACEMENT

[75] Inventors: Harlan C. Amstutz, Pacific Palisades; Ian C. Clarke, Santa Monica, both of Calif.

[73] Assignee: Regents of the University of California, Berkeley, Calif.

[21] Appl. No.: 764,184

[22] Filed: Jan. 31, 1977

[51] Int. Cl.² ............................................. A61F 1/24
[52] U.S. Cl. ................................... 3/1.912; 128/92 C
[58] Field of Search ................... 3/1.9, 1.91, 1.912, 3/1.913; 128/92 C, 92 CA

[56] References Cited

U.S. PATENT DOCUMENTS

| | | | |
|---|---|---|---|
| 2,668,531 | 2/1954 | Haboush | 128/92 CA |
| 3,829,904 | 8/1974 | Ling et al. | 3/1.912 |
| 3,925,824 | 12/1975 | Freeman et al. | 3/1.912 |
| 4,035,848 | 7/1977 | Wagner | 3/1.913 |

OTHER PUBLICATIONS

"Trapezoidal-28 Total Hip Prostheses" and "The Trapezoidal-28 Total Hip Replacement" by H. C. Amstutz, Zimmer Catalog, Zimmer USA, Warsaw, Indiana, p. A 14-1(Rev 2), 1974, pp. D-11 thru D-20, Feb. 1973, Scientific Library.

*Primary Examiner*—Ronald L. Frinks

*Attorney, Agent, or Firm*—Poms, Smith, Lande & Glenny

[57] ABSTRACT

In the replacement of the hip joint, full access to the hip joint is obtained by separating the trochanter, a large protuberance on the upper portion of the upper leg bone, or femur, from the remainder of the femur, and the subsequent dislocation of the hip joint. Following dislocation, a minimum amount of bone is removed from the femoral ball and sufficient bone is removed from the socket to accommodate the minimum thickness surface replacement elements. A thin hollow inert metal ball or shell member having an outer diameter close to that of the original hip joint is then cemented onto the upper end of the femur, and an ultra high molecular weight polyethylene cup is cemented into the hip bone socket, with acrylic bone cement. To achieve maximum strength with minimum thickness, both the metal and plastic surface elements, although spherical at their mating surfaces, are thicker at their maximum load bearing points toward the top, and are of lesser thickness elsewhere. The two joint surface elements which are both generally hemispherical, have inner and outer surfaces which are both eccentric and asymmetric, with the thicker portion of the plastic liner being about 45° off the central hemispherical axis, and the thicker portion of the metal shell being its upper portion.

24 Claims, 6 Drawing Figures

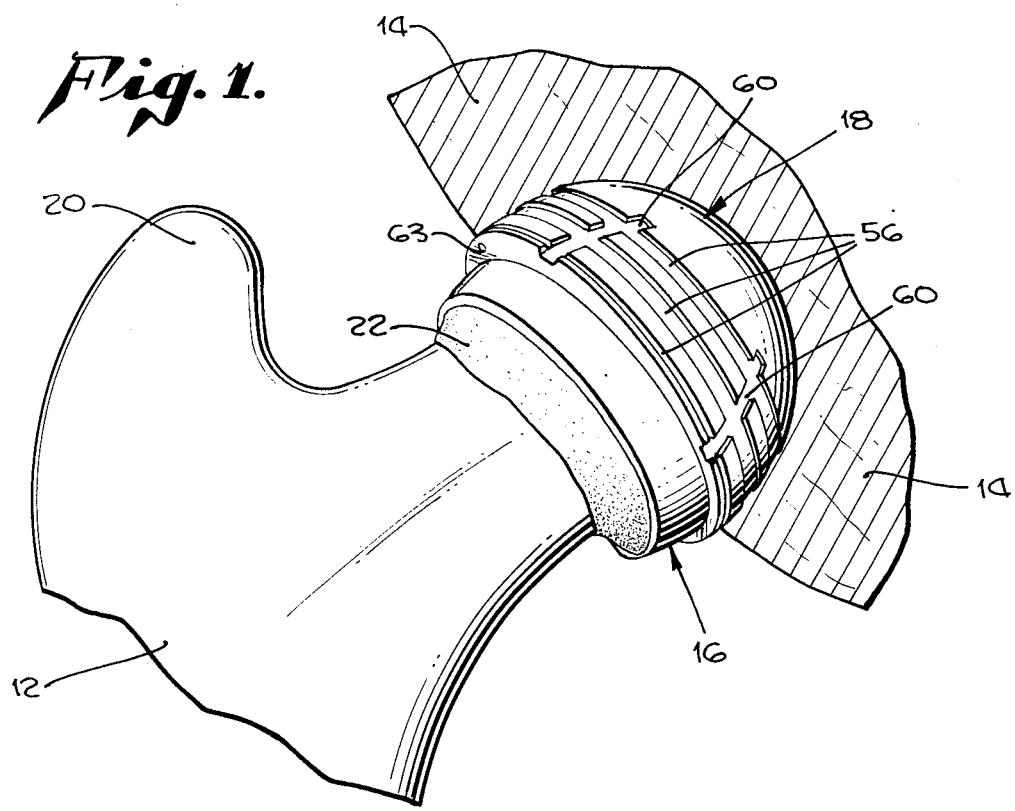
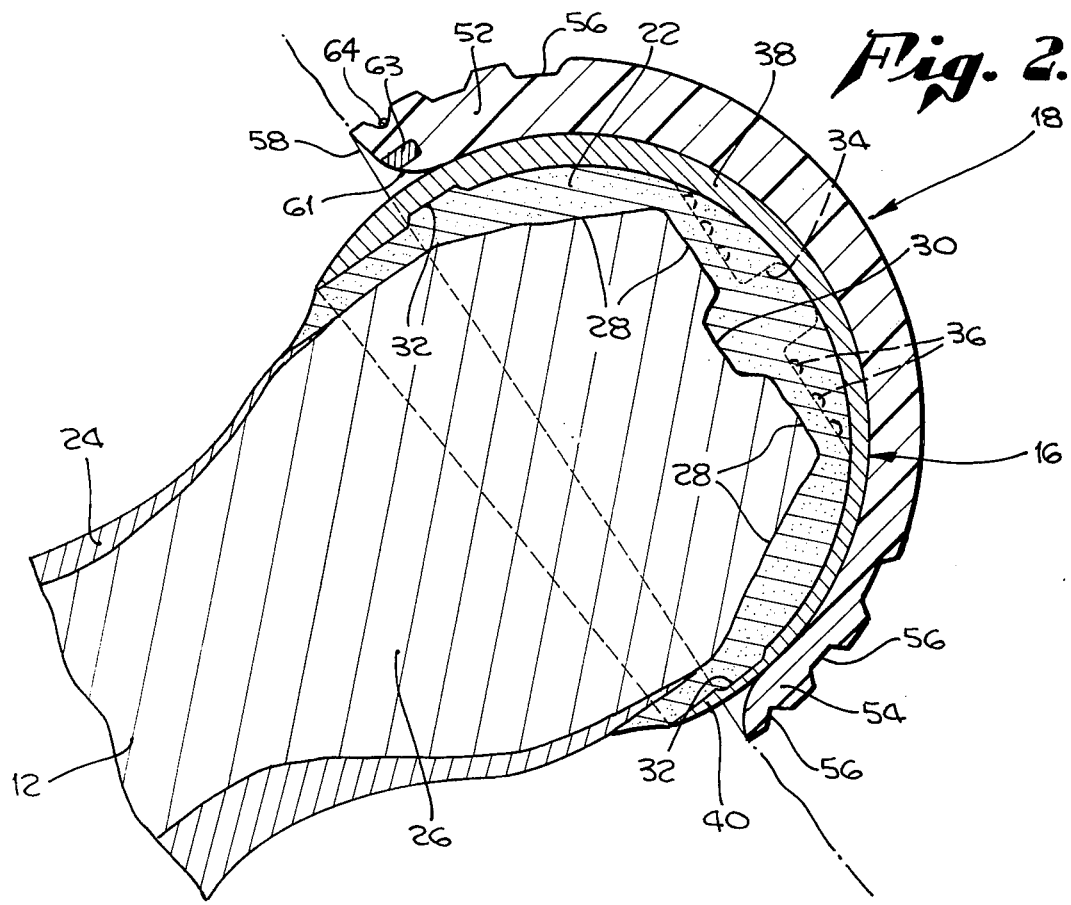

TOTAL HIP JOINT REPLACEMENT

FIELD OF THE INVENTION

This invention relates to the total replacement of the hip joint surfaces.

BACKGROUND OF THE INVENTION

Problems with diseased and arthritic hip joints have been with the human race for many years. Since early in the present century, various proposals and operative techniques have been proposed for partial or complete replacement of the hip joint. Some of the initial efforts at total hip replacement involved materials problems. Other of the more recently popular proposals for total hip joint replacement have involved the removal of substantial amounts of bone, either from the upper end of the femur, (the large upper leg bone), or from the hip socket or both. One of the more widely used techniques has involved the removal of the upper end of the femur and the use of a metal ball, somewhat smaller than the original ball at the upper end of the femur, mounted on a long pointed metal stem which was forced into the upper end of the femur with the pointed stem extending down and being secured in the intramedullary canal.

Incidentally, relative to the structure of the femur it has a dense "cortical" outer surface or shell, a porous "cancellous" structure just within the outer shell, and the central "intramedullary canal" in which the bone marrow and blood vessels, for example, are located.

Unfortunately, significant problems have been encountered with a number of prior total hip joint replacement techniques. More specifically, with regard to the femoral replacements of the metal stem type mentioned above, a number of cases of loosening and/or of breaking of the metallic ball-and-stem member have been encountered. Not only does a loosened or fractured stem create pain and hence lack of function but also the bone destruction created by the removal of the broken components constitutes a considerable problem for any future hip-joint salvage. In general it is believed that the excess amount of bone removal which has occurred in many prior operative techniques for hip joint replacement has been responsible for a higher incidence of medical problems than might otherwise be encountered.

In addition, it may be noted that it has previously been proposed to locate the socket in the plastic member which is secured in the hip, below center, to provide increased strength in the upper portion of tghe plastic socket member.

A principal object of the present invention is to provide a total hip joint replacement technique and structure which will involve a minimum removal of bone from the ball at the upper end of the femur and insure the fit of the plastic liner within the acetabular bone, or hip socket. A further object of the present invention is to maintain substantially the same diameter of ball and socket in the replacement, as was present in the original ball and socket of the patient. In this way more natural and more complete movement of the joint may be achieved and the customary "dead-space" normally created by conventional stem-type hip replacements is eliminated.

SUMMARY OF THE INVENTION

The present technique involves the concept of total hip joint replacement in which a minimum amount of bone is removed both from the ball at the upper end of the femur, yet still permits adequate fitting of the plastic liner within the acetabular bone, or hip socket.

One aspect of the invention involves the use of a hemispherical ball surfacing element or shell made of metal, and a mating hemispherical socket element made of a strong wear-resistant plastic. In each case the surfacing element is relatively thin and has a smooth spherical surface with a clearance, of about 0.004–0.012 inch (0.1–0.3 mm) between the mating spherical surfaces designed to minimize friction and wear. Both elements are of course made of the best biologically acceptable materials available. Also, the metal-ball surfacing element is selected to provide a close fit over the upper end of the femur following removal of the diseased or impaired surface of the original bone by precision reaming techniques, and this is usually with a ball surfacing member having an outer diameter approximating the original diameter of the natural ball and socket joint. For each size of ball surfacing element a series of several socket members are provided to accommodate the amount of bone which has been removed. If very little bone has been removed, the thinest form of plastic socket liner with adequate strength if provided, while thicker plastic cups are provided when more bone has been removed from the surface of the hip socket.

One aspect of the invention involves the use of a thin metal ball surfacing element which is slightly more than hemispherical in extent. In addition, the ball surfacing element may be provided with equatorial and polar grooves to assist in its cementing into place firmly and securely. The entire metal surfacing element is relatively thin, and is preferably less than 10 millimeters in thickness at its maximum thickness region, with the average thickness being equal to perhaps 2 mm or 3 mm. The maximum wall thickness of the metal ball surfacing element or member (apart from the dome), is displaced vertically from the center of the unit to provide maximum strength in the load bearing region of the hip joint. The medial portion of the metal ball surfacing element is relatively thick about 5 mm to 10 mm and may be provided with deep grooves extending in different directions to facilitate firm securing in position.

The thicker dome at the center of the metal shell provides a number of functions. First, the diseased bone normally present in this area can be trimmed away without requiring the use of excess quantities of cement as a filler. Its non-circular contour provides a keying action against the precision-reamed bone. The thick dome permits deep fixation channels and also contributes to the high mechanical strength of the metal shell.

In accordance with a method of total hip joint replacement, following dislocation of the hip joint, a minimum amount of bone is removed from the surface of the head of the femur and from the surface of the pelvis hip joint socket to expose healthy, firm bone surfaces, ball and socket surfacing members of the form outlined above are cemented into position to provide a replacement hip joint surface having a ball of substantially the same size and in substantially the same location as the original hip joint, and the metal ball and the plastic socket members are relocated in engagement with one another.

The present technique has the advantage of simulating the natural hip joint action by duplicating the location and diameter of the original hip joint as closely as possible. In addition to removing a minimum amount of bone, problems involving the loosening of the joint replacement elements are minimized, and problems of breaking of the stem type units are avoided.

Another medical technique which may be employed in the hip joint surface replacement method contemplated by the present invention involves facilitation of dislocation of the hip joint by removing the trochanter, a major protruberance near the upper end of the femur to which a number of muscles and ligaments are secured. This permits good visualization of the hip joint for safe bone reaming techniques, thus safeguarding the integrity of the femoral neck, and also facilitates the optimal orientation of components during cementation in the bone. When the trochanter is temporarily separated from the main portion of the upper leg bone, the hip joint may be relatively easily dislocated; then, when the new ball and socket surfaces have been cemented into position, they are relocated into proper position and the trochanter is pinned back onto the femur. After a short period of time the bone mends, and full strength and mobility returns to the leg and hip joint at a relatively early date.

Other objects, features, and advantages of the present invention will become apparent from a consideration of the following detailed description and from the associated drawings.

BRIEF DESCRIPTION OF THE DRAWINGS

FIG. 1 is an overall view of the surface replacement hip joint technique of the present invention;

FIG. 2 is a detailed showing of the cross section of the upper end of the femur, the metal cap secured in position, and the matching plastic socket surfacing member;

DETAILED DESCRIPTION

Figure 3:
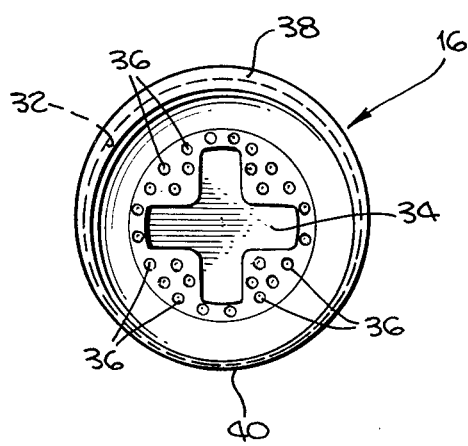
FIGS. 3 and 4 are inner and side views of the metal femoral shell.

Referring to the drawings, FIG. 1 shows the upper end of the large upper leg bone, of femur 12, and the pelvis 14 with the metal femoral cap 16 and the mating plastic acetabular cup 18 shown in position. Near the upper end of the femur 12 is a large protruberance 20 known as the trochanter. As noted above, full access to the hip joint is obtained by separating this protruberance, the trochanter, from the remainder of the femur. Because many of the major muscles which control the movement of the leg, and which holds the ball at the upper end of the femur into the hip bone socket, are attached to the trochanter, its separation permits relatively easy dislocation of the hip joint, and access to the diseased surfaces of an arthritic or otherwise diseased hip joint.

FIG. 2 is a cross-sectional view of the upper end of the femur with the metal cap 16 cemented into place with the acrylic cement 22 and located inside the acetabular cup 18. In FIG. 2 the harder outer bone surface 24 is shown in one form of cross sectioning, while the inner portion of the bone 26 is shown with different cross sectioning. The original surfaces of the end of the femur have been reamed with a hollow cylindrical and a tapered reamer so that healthy bone surfaces 28 are exposed. In addition, a relatively shallow groove 30 has been cut into the upper end of the femur for keying or locking with the cement 22 which secures the metal femoral cap or shell 16 to it. The metal shell 16 extends over a surface which is somewhat greater than a hemisphere and has an "equatorial" groove 32 and other irregularities on its inner surface to lock with the cement. The high density plastic member 18 has an inner diameter which is approximately 0.1 to 0.3 mm. larger than the outer diameter of the metal cap 16, and has a channelled outer surface for cementing into the hip socket in the pelvis.

The configuration of the metal femoral shell 16 and the acetabular cup member 18 will now be considered in greater detail in connection with FIGS. 3, 4, 5, and 6.

Figure 4:
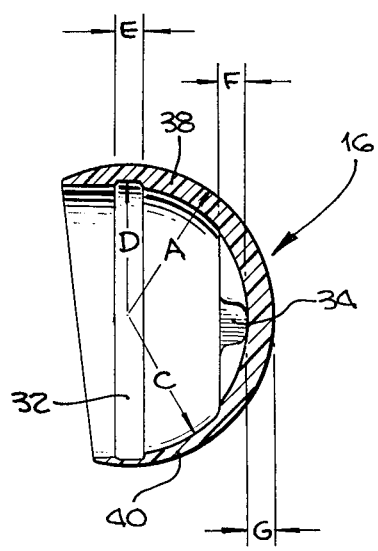

With reference to FIGS. 3 and 4, the metal shell 16 is relatively thin, with its maximum thickness being approximately 7 mm. at the medial or central region. In this domed or medial region it is provided with two major intersecting grooves which are about 3 mm. deep and which form the cross 34 shown in FIG. 3. In addition, the medial area is provided with a large number of dimples or holes 36 which help to fix the cap firmly in position.

Before considering other details of the metal cap and the matching plastic cup, reference will be made to Tables I and II.

TABLE NO. I

| Type | | SR-1 | SR-2 | SR-3 | SR-4 | SR-5 |
|---|---|---|---|---|---|---|
| Femoral | I.D. | 32 mm | 35 mm | 39 mm | 43 mm | 47 mm |
| Cap | O.D. | 36 mm | 39 mm | 43 mm | 47 mm | 51 mm |
| Cup | I.D. | 36 . 1 mm | 39 . 1 mm | 43 . 1 mm | 47 . 1 mm | 51 . 1 mm |
| Small | O.D. | 44 mm | 47 mm | 51 mm | 55 mm | 59 mm |
| Medium | O.D. | 46 mm | 49 mm | 53 mm | 57 mm | 61 mm |
| Large | O.D. | 48 mm | 51 mm | 55 mm | 61 mm | 63 mm |

TABLE NO. II

FEMORAL CAP DIMENSIONS
LETTER DESIGNATIONS APPEAR IN FIG. 4

| CAP. NO. | A | C | D | E | F | G |
|---|---|---|---|---|---|---|
| SR-1 | 18 | 16 | 16 . 625 | 4 | 3 | 4 |
| SR-2 | 19 . 5 | 17 . 5 | 18 . 125 | 4 | 3 | 4 |
| SR-3 | 21 . 5 | 19 . 5 | 20 . 125 | 4 | 3 | 4 |
| SR-4 | 23 . 5 | 21 . 5 | 22 . 125 | 4 | 3 | 4 |
| SR-5 | 25 . 5 | 23 . 5 | 24 . 125 | 4 | 3 | 4 |

Supplemental Notes to Dimension Tables I and II

Note 1. Plastic Cup I.D. dimensions are from 0.1 to 0.3 larger than metal cap O.D. dimensions, but only the minimum cup I.D. dimension is given.

Note 2. The center for radius C is located 0.5 mm below the center for radius A, to give increased thickness to the upper wall.

Figure 6:
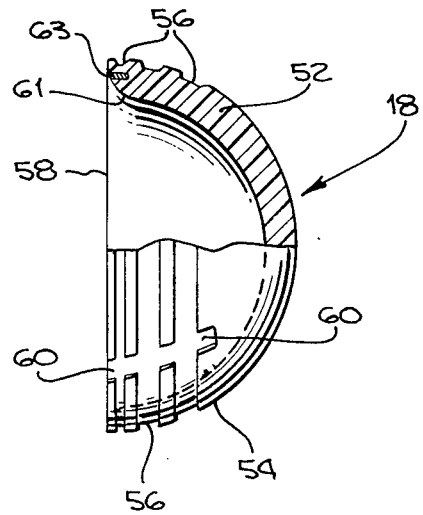

Note 3. The center for the I.D. of the plastic cups is located 1.0 mm from the center for the I.D., and is displaced at an angle of 45° from the axis of the cup downward and to the left as the cup is shown in FIG. 6.

In Table No. I set forth above the inner and outer diameters for the five different sizes of femoral caps, designated SR-1 through SR-5, are listed. Incidentally, the designation "SR" refers to the different series of "surface replacement" units. The dimensions for the various metal caps range from an outer diameter of 36.1 mm for SR-1 up to 51 mm for SR-5.

For each of the five sizes of metal caps, there are three acetabular cups of different thicknesses. Thus, for example, for the SR-1 femoral cap the I.D. of each of the three mating acetabular cups would be 36.1 mm to 36.3 mm and they would be provided with outer diameters of 44 mm, 46 mm, and 48 mm. The minimum average thickness in the load-bearing portion of about 5 mm is chosen to provide adequate strength even for the thinnest plastic liner. In a similar manner each of the other four sizes of metal femoral caps is provided with a set of three mating plastic cups, each having a proper corresponding I.D., and varying thicknesses. Table II sets forth various dimensions for each of the five sizes of femoral caps, with the letters in Table No. II corresponding to those which appear in FIG. 4.

It may be noted in connection with FIG. 4 that the upper portion 38 of the metal shell 16 is thicker than the lower portion 40. Similarly, with reference to FIG. 6 the upper portion 52 of the high density plastic cup is thicker than the lower portion 54. In each case the thicker upper portions are in the superior or higher load-bearing areas of the hip ball and socket joint and provide the greater strength in this region which is necessary, as compared with the guiding function performed by the lower regions 40 of the femoral cap, and 54 of the mating cup. Consistent with the desire to remove a minimum amount of bone, and to provide a ribbed or otherwise irregular surface for securing through medical cement to the bone, there is only a limited space available. Accordingly, by making both the femoral cap and the mating cup eccentric with greater thickness and strength in their superior portions, a longer-lasting hip joint may be achieved.

Returning to FIGS. 3 and 4, in addition to the dimensions set forth in Table No. II, it may be noted that the equatorial groove 32 is 1 mm in depth. The minimum thickness of the shell 16 in the lower region at the bottom of the groove 32 is 1.25 mm. In the upper portion of the metal shell 16, the minimum thickness is 2.5 mm at the bottom of groove 32. The width of each of the grooves which cross to form recess 34 is approximately 6 mm.

Incidentally, a considerable number of tests were performed using the acrylic bone cement mentioned above and various forms of irregularities on the inner surface of the femoral cap. Strength tests were performed to determine failure of the bone structure and the cap cement and head joint. The design shown in FIGS. 3 and 4 represents a structure having an interface fixation strength compatible with and very near equal to the bone strength under the mechanical tests which were performed to simulate realistic conditions.

Figure 5:
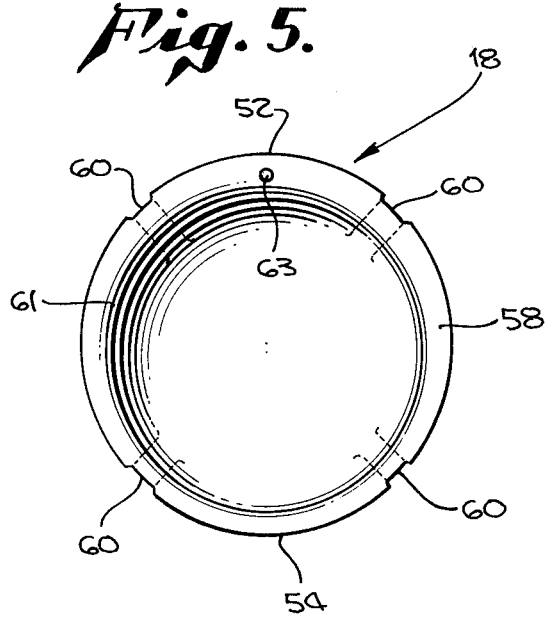
FIGS. 5 and 6 are two views of the matching high density plastic socket liner, or acetabular component.

With reference to FIGS. 5 and 6, the inner diameter and the outer diameter for the plastic cup has been set forth above in Table No. I. The center for the inner diameter is displaced 1 mm from the center for the outer diameter below and to the left at an angle of 45° in the orientation shown in FIG. 6. In certain areas, therefore, the lower wall 54 is about 2 mm thinner than the certain areas of the upper wall 52. In addition, the angle for maximum eccentricity and therefore maximum thickness in FIG. 6 is approximately 45° above the central axis of the cup. The outer surface of the cup 18 shown in FIGS. 5 and 6 is provided with a series of peripheral grooves 56 which are generally parallel to the edge 58 of the hemisphere. In addition, a series of grooves 60 are provided which extend generally perpendicular to the edge of the hemisphere and these sets of grooves provide both rotational and translational keying with the cement to avoid turning or inadvertent loosening of the cup from the pelvic socket. To avoid interference with the femur, the cup 18 may be precisely hemispherical, or may be a millimeter or two less than hemispherical in extent. The four grooves 60 are spaced equally around the plastic liner 18 and each of the two upper grooves are displaced by 45° from the main load bearing, and thickest top portion of the liner 18. It may also be noted that a metallic radiographic marker 63 is located in the central upper portion of the rim of the plastic liner for both visual and subsequent X-ray identification of the orientation of the liner. Similarly, a thin wire 64 may extend most of the way around the outer groove of plastic liner 16 for X-ray purposes.

The inner edge 61 of the plastic liner 18 is relieved to avoid early interference with the metal shell or the femur and to insure a full range of movement.

For completeness and to permit easier practice of the present invention by those skilled in the art, a brief statement of the medical procedure in medical terms will now be presented:

Medical Procedure

A standard transtrochanteric approach is employed with the patient in the lateral decubitus position. A lateral skin incision was made longitudinally centered over the greater trochanter, extending proximally and distally 10 cm with the proximal leg curved slightly posteriorly. The fascia lata was divided along the line of the incision and the anterior and posterior borders of the gluteus medius defined. The joint was aspirated and the sample sent for culture. A longitudinal incision of about 20 cm was made in the anterosuperior capsule and the Gigli saw passer was positioned over the superior femoral neck, taking care not to score the neck, and was brought out at the posterior border of the gluteus medius. The greater trochanter was removed and hemostasis was obtained from the vessels of the trochanteric crusiate anastomosis. The greater trochanteric fragment with the attached gluteus medius was then reflected proximally and held out of the way with three Steinman pins placed through the ilium 20 mm apart and 20 to 30 mm above the superior acetabular rim. Measurements were made from the rim to a point on the greater trochanteric fragment to determine any change in leg length. A longitudinal incision was then made with care not to cut the femoral neck, along the superior portion of the capsule and ilio-femoral ligament extending from the osteotmized greater trochanter to the acetabular margin. The anterior capsular ligamentous complex was then released by sharp dissection from the intertrochanteric line to within 20 mm or so of the lesser trochanter, staying close to bone. Posteriorly the capsule and the remaining insertions of the short rotators were again incised from the capsule, out close to femoral bone. This dissection was carried out minimally to allow anterior dislocation of the femoral head, which might have required transection of the ligamentum teres with the ligamentum teres cutter. In addition, all tissues were dissected close to bone to minimize any danger to various blood vessels and nerves.

After dislocation, those portions of the labrum and capsule-ligamentous complex are freed from the bony acetabular rim sufficiently to allow an uninterrupted view of the acetabulum. Specimen is then taken from the cotyloid foramen for culture.

Radiographic templates of the surface-replacement design provided the basic guidelines for determining which size (SR-1 through SR-5) was the most appropriate. The acetabulum was then deepened, using the appropriate size of Mira reamers. Three or more keying or fixation holes, approximately ½ inch in diameter are then drilled into the reamed bony surface of the acetabulum. The femoral side was prepared by driving a wire centrally into the head as a guide for alignment with the axis of the femoral neck. A chamfer reamer then followed this wire and bevelled the equatorial aspect of the head in preparation for the cylindrical reamers. In reaming the femoral head the larger sizes of cylindrical cutters were always used first, so that improved alignment could be obtained, to be followed with successively smaller reamers. The aim here was neither to encroach upon the sites of the entrant blood vessels in the femoral neck/head region nor to undercut the neck itself. It was for these reasons that a range of five sizes of carefully graduated surface-replacements was designed for custom fitting of each patient's femoral head.

Reaming of the femoral head to the optimal depth requires consideration of sclerotic or cystic bone. The objective is to uncover healthy bleeding bone with minimal removal of bone tissue. To this end we employed combined reamer and saw guides for use on the femoral head. Each guide indicated the bone depth required to fit the shell interior and acted as a saw guide for sectioning the medial dome of the femoral head.

At this stage, the final size of replacement was determined by consideration of the sizes of both the femoral and acetabular sites. The criterion here was that the acetabular socket and acrylic should be fully supported by bone for optimal coverage, i.e., the cup should neither be allowed to protrude significantly from the acetabulum nor to penetrate the medial acetabular wall. The anthropometric study had indicated that, with the typical acetabular dimensions and associated reaming procedure, a hemispherical polyethylene liner would generally be well supported. A trial reduction is performed before cementing either component, and the range of movement is carefully assessed. The acetabulum was then cemented, using early insertion of the acrylic to achieve good fixation of the plastic liner. A waterpick was used to remove debris and blood clots from the femoral head. The metal femoral cup was cemented on and aligned more or less in neutral position with respect to the femoral-neck axis depending on the range of motion analysis during the trial reduction, and excess acrylic was trimmed from the shell margins. The joint was reduced and the range of motion analyzed.

Concerning another phase of the present invention, the matter of materials should be mentioned again. A number of high strength biologically inert metals are now known. However, a cast cobalt chromium molybdenum shell is preferred for the femoral cap. The cup-shaped matching member should be of ultra-high molecular weight polyethylene, or other comparable high-strength plastic. The cement should be acrylic cement prepared for medical purposes and available from several medical suppliers.

With regard to related prior work of others, reference is also made to U.S. Pat. No. 3,925,824, granted Dec. 16, 1975, entitled "Endoprosthetic Bone Joint Devices", inventor, M. A. R. Freeman et al. While the components disclosed in this patent are precursors of the present invention, the concept of removing a minimum amount of bone does not appear to be present as the femoral cap and the acetabular cup members disclosed in this patent appear to be unduly thick. Also, there appears to be no disclosure of making the femoral cap, for example, thicker in the upper load-bearing area and of reduced thickness in the lower portion, to permit removal of lesser amounts of bone from the femoral joint surfaces.

Concerning the direction of maximum eccentricity and thickness, the presently preferred angle is approximately 45° from the central axis for the plastic liner; and 90° for the upper surface of the metal shell which is of course of greater extent. The important factor is to increase the strength of the upper load bearing portions of both members. In addition, the average thickness of the femoral cap is approximately 1½ to 2½ mm, with the exception of the domed portion, and it is believed that significantly improved results over prior techniques may be achieved with an average thickness less than 6 mm. It is also noted that the femoral cap is slightly greater than hemispherical in extent, with the superior edge extending approximately 6 mm beyond the "equatorial" plane and the lower edge of the cap extending about 3 mm beyond this plane. This additional coverage on the upper or superior face permits increased articulation with continued engagement of the metal shell and plastic liner.

In conclusion, the present invention contemplates a new complete hip replacement technique involving minimum bone removal and the use of a very thin femoral cap together with a matching high density plastic cup member to form a newly surfaced hip joint with substantially the same size and corresponding range of movement as the original joint. It is to be understood that minor departures from the specific disclosure are still within the present invention.

We claim:

1. A method of total hip joint replacement involving a minimum removal of bone from a patient's hip joint surfaces comprising:

separating the trochanter from the remainder of the femur;

dislocating the hip joint to expose the diseased joint surfaces;

removing a minimum amount of diseased bone from the surface of the head of the femur, and from the surface of the pelvis hip joint socket to expose healthy firm bone surfaces;

selecting an entirely thin walled asymmetric, eccentric, substantially hemispherical biologically inert metal shell having an outer diameter substantially equal to the original diameter of the mating ball and socket surfaces of the patient's hip joint with the inner surface of said metal shell being free of inwardly directed extended protrusions;

cementing said thin metal shell over the head of the femur, with a continuous uncompartmentalized layer of cement;

and with the thicker portion of the metal shell located at the superior or load bearing area of the head of the femur;

selecting an asymmetric eccentric substantially hemispherical high strength biologically inert plastic liner having an inner diameter giving minimum clearance relative to the outer diameter of said metal shell, and having a thickness approximately equal to the thickness of the diseased bone layer which was removed;

cementing said plastic liner into the hip socket with the thicker portion of sais plastic liner being oriented at the superior or load bearing area of the socket;

engaging said metal shell and plastic liner; and securing the patient's trochanter onto the femur.

2. A method as set forth in claim 1 further comprising the step of cutting a shallow groove in the end of the head of the femur, whereby the cementing step will produce a positive interlock against rotation.

3. A method as set forth in claim 1 further including the step of utilizing a liner which is made of high molecular weight plastic.

4. A method as set forth in claim 1 further comprising the step of providing indentations in the central inner surface of said metal shell, and causing the cement to flow into said indentations to positively lock said metal shell against rotation.

5. A method as set forth in claim 1 further including the step of providing peripheral and substantially equatorial grooves in the inner surface of said metal shell and the outer surface of said plastic liner, and flowing cement into said grooves to secure said shell and liner against displacement from the bones to which they are secured.

6. A set of artificial ball and socket hip joint surface units comprising:

an entirely thin walled asymmetric, eccentric substantially hemispherical, biologically inert metal shell having a smooth spherical exterior surface, and a grooved and dimpled internal surface, free of inwardly directed extended protrusions; the upper side of said shell to be located on the load bearing portion of the joint being substantially thicker than the lower side of said shell; and a plurality of thin asymmetric eccentric substantially hemispherical inert plastic liners, each having a smooth internal spherical surface to match the exterior surface of said shell with minimum clearance, each said liner having a thicker area on its upper side to be located at the upper load bearing portion of the joint, each of said liners being of a different thickness to approximate the amount of bone which may be removed from the hip socket, to locate the artificial hip joint in substantially the original hip joint diameter, each said liner being provided with external irregularities for locking each said liner in place.

7. A set of surface units as defined in claim 6 wherein said thin metal shell is slightly more than hemispherical in extent.

8. A set of surface units as defined in claim 6 wherein said metal shell has an upper thicker surface which extends beyond the hemispherical size by several millimeters.

9. A set of surface units as defined in claim 6 wherein the upper side of said metal shell averages between 1½ mm. and 4 mm. in thickness.

10. A set of surface units as defined in claim 7 wherein said metal shell is provided with an equatorial groove on its inner surface.

11. A set of surface units as defined in claim 6 wherein said thin metal shell has a central dome which is at lease 5 mm. in thickness, and which is internally grooved to a depth of at least 2 mm.

12. A set of surface units as defined in claim 6 wherein each said plastic liner is provided with grooves parallel to the edge of the hemisphere and additional grooves substantially perpendicular thereto, on the outer surface of said liner.

13. An artificial surfacing for hip joints for mounting on the upper end of the femur comprising:

a thin eccentric, asymmetric substantially hemispherical, biologically inert metal shell having a smooth spherical exterior surface, and an internal surface which includes interlocking recesses and grooves;

said metal shell having an upper side wall which is substantially thicker than its lower side wall, the maximum thickness of said metal shell being less than 10 millimeters; and said metal shell having a spherical extend slightly greater than hemispherical, and being provided with an inner groove extending generally parallel to its edge to facilitate firm securing of the shell in position, and said shell being free of inwardly directed extended protrusions, whereby said shell will interlock with but not divide or compartmentalize cement with which it may be used.

14. An artificial surfacing for hip joints as defined in claim 13 wherein the thicker upper side wall of said metal shell is of greater extent than the lower thinner side wall.

15. An artificial surfacing for hip joints as defined in claim 13 wherein the inner surface of said metal shell member is provided with deep medial fixation channels to key against movement of the metal shell relative to the femur.

16. An artificial surfacing for hip joints as defined in claim 13 wherein the average thickness of the wall of said metal shell is less than five millimeters.

17. An artificial ball surfacing for hip joints as defined in claim 12 wherein said shell extends beyond the hemispherical to the greatest extent and by at least three millimeters in the upper region aligned with the thickest portion of said shell.

18. A method of total hip joint replacement involving a minimum removal of bone from a patient's hip joint surfaces comprising:

dislocating the hip joint to expose the diseased joint surfaces;

reaming a minimum amount of diseased bone from the surface of the head of the femur with precision cylindrical and tapered reamers, and from the surface of the pelvis hip joint socket to expose health firm bone surfaces, selecting a thin asymmetric, eccentric, substantially hemispherical biologically inert metal shall having an inner diameter matched to the size of said cylindrical and tapered reamers, and an outer diameter substantially equal to the original diameter of the mating ball and socket surfaces of the patient's hip joint, and with the inner surface of said metal shell being free of inwardly directed extended protrusions;

cementing said thin metal shell over the head of the femur, with the thicker portion of the metal shell located at the superior or load bearing area of the head of the femur;

selecting an asymmetric eccentric substantially hemispherical high strength biologically inert plastic liner having an inner diameter giving minimum clearance relative to the outer diameter of said metal shell, and having a thickness approximately equal to the thickness of the diseased bone layer which was removed;

cementing said plastic liner into the hip socket with the thicker portion of said liner being oriented at the superior or load bearing area of the socket; and engaging said metal shell and plastic liner.

19. A method as defined in claim 18 further comprising the steps of:

providing fixation or keying irregularities in the end of the femur, the reamed surface of the hip joint socket, the inner surface of the metal shell, the outer surface of the plastic liner; and flowing cement into said keying or fixation irregularities to firmly secure said metal shell to the end of the femur and said plastic liner into the hip joint socket.

20. A set of surface units as defined in claim 12, wherein said grooves extending perpendicular to the edge of said plastic liner are located on either side of the superior, thickest portion of said liner.

21. A set of surface units as defined in claim 6 wherein metallic means are located at the edge of said plastic liner aligned with the thickest portion of said liner for visual and X-ray position determination.

22. An artificial surfacing for hip joints as defined in claim 13 wherein the side walls of said shell away from said dome average less than 3 mm in thickness.

23. A set of surface units as defined in claim 21 wherein said metallic means includes a wire extending at least partially around said plastic liner adjacent its edge.

24. A set of surface units as defined in claim 21 wherein a metal stud is located at one point around the periphery of said plastic liner near the edge thereof.

* * * * *